(12) United States Patent
Schmidt

(10) Patent No.: US 7,013,896 B2
(45) Date of Patent: Mar. 21, 2006

(54) MASK WITH INHALATION VALVE

(75) Inventor: James N. Schmidt, London (CA)

(73) Assignee: Trudell Medical International, London (CA)

(*) Notice: Subject to any disclaimer, the term of this patent is extended or adjusted under 35 U.S.C. 154(b) by 429 days.

(21) Appl. No.: 10/139,992

(22) Filed: May 6, 2002

(65) Prior Publication Data

US 2002/0170557 A1    Nov. 21, 2002

Related U.S. Application Data

(60) Provisional application No. 60/289,485, filed on May 8, 2001.

(51) Int. Cl.
*A62B 7/10* (2006.01)

(52) U.S. Cl. ............................ 128/206.15; 128/207.12; 128/203.29

(58) Field of Classification Search ........... 128/204.11, 128/204.12, 205.25, 206.15, 207.12, 203.11, 128/203.28, 203.29
See application file for complete search history.

(56) References Cited

U.S. PATENT DOCUMENTS

| | | | |
|---|---|---|---|
| 217,691 A | 7/1879 | Hurd | |
| 302,949 A | 8/1884 | Skene | |
| 346,367 A | 7/1886 | Genese | |
| 374,831 A | 12/1887 | Harrington | |
| 379,042 A | 3/1888 | Battershall | |
| 440,713 A | 11/1890 | Krohne et al. | |
| 533,127 A | 1/1895 | Horton | |
| 590,376 A | 9/1897 | Pickin | |
| 731,973 A * | 6/1903 | Teter ..................... | 128/207.13 |
| 733,027 A * | 7/1903 | Goldan .................. | 128/203.25 |
| 756,357 A | 4/1904 | Gunnell | |
| 812,706 A * | 2/1906 | Warbasse ............... | 128/207.13 |
| 1,007,644 A * | 10/1911 | Cocke .................... | 128/207.12 |
| 1,221,387 A * | 4/1917 | Ste Marie .............. | 128/207.12 |
| 1,671,010 A | 5/1928 | Braecklein | |
| 1,695,170 A | 12/1928 | Burdick | |
| 1,998,327 A | 4/1935 | McGuire | |
| 2,029,129 A | 1/1936 | Schwartz | |
| 2,070,241 A | 2/1937 | Schwartz | |
| 2,164,330 A | 7/1939 | Katz et al. | |
| 2,238,964 A | 9/1941 | Benos | |
| 2,344,669 A * | 3/1944 | Barker et al. .......... | 128/206.15 |
| 2,381,568 A | 8/1945 | Booharin | |
| 2,432,946 A | 12/1947 | Theunissen | |
| 2,445,347 A | 7/1948 | Ehlinger | |
| 2,843,119 A | 7/1958 | Glasser | |
| 2,848,994 A | 8/1958 | Aguado | |
| 2,888,012 A * | 5/1959 | Larson ................... | 128/207.12 |
| 2,893,387 A * | 7/1959 | Gongall et al. ........ | 128/206.15 |
| 2,931,356 A | 4/1960 | Schwarz | |

(Continued)

FOREIGN PATENT DOCUMENTS

AR        244490        11/1993

(Continued)

Primary Examiner—Aaron J. Lewis
(74) Attorney, Agent, or Firm—Brinks Hofer Gilson & Lione

(57) ABSTRACT

A mask for use in inhaling a substance includes a mask housing defining a chamber. The housing has an inlet and an outlet communicating with the chamber. A valve is disposed in the inlet and is integrally formed with the housing, such that the valve and the housing are formed as a one-piece unit. In a preferred embodiment, the housing further comprises an exhaust port and an exhalation valve disposed in the exhaust port, with a shield disposed around the exhaust port. In another aspect, a method of manufacturing a mask also is provided.

22 Claims, 2 Drawing Sheets

U.S. PATENT DOCUMENTS

| | | | |
|---|---|---|---|
| 2,985,169 A | 5/1961 | Elling | |
| 3,027,896 A | 4/1962 | Newton | |
| 3,124,124 A * | 3/1964 | Cross | 128/203.11 |
| 3,182,659 A | 5/1965 | Blount | |
| 3,232,292 A | 2/1966 | Schaefer | |
| 3,490,452 A | 1/1970 | Greenfield | |
| 3,491,755 A | 1/1970 | Barghini et al. | |
| 3,556,122 A * | 1/1971 | Laerdal | 137/102 |
| 3,707,966 A | 1/1973 | Nebel | |
| 3,889,671 A * | 6/1975 | Baker | 128/207.13 |
| 4,002,167 A | 1/1977 | Rambosek | |
| 4,016,878 A | 4/1977 | Castel et al. | |
| 4,071,026 A * | 1/1978 | Bevins | 128/205.29 |
| 4,080,664 A | 3/1978 | Morris et al. | |
| 4,470,412 A | 9/1984 | Nowacki et al. | |
| 4,546,768 A | 10/1985 | Ferierabend | |
| 4,573,463 A | 3/1986 | Hall | |
| 4,637,387 A | 1/1987 | Hall | |
| 4,705,033 A | 11/1987 | Halfpenny | |
| 4,722,334 A | 2/1988 | Blackmer et al. | |
| 4,770,169 A | 9/1988 | Schmoegner et al. | |
| 4,809,692 A | 3/1989 | Nowacki et al. | |
| 4,811,730 A * | 3/1989 | Milano | 128/203.11 |
| 4,819,628 A * | 4/1989 | Eisenberg et al. | 128/203.11 |
| 4,832,015 A | 5/1989 | Nowacki et al. | |
| 4,850,346 A | 7/1989 | Michel et al. | |
| 4,858,605 A * | 8/1989 | Levy | 128/203.11 |
| 4,865,027 A | 9/1989 | Laanen et al. | |
| 4,886,055 A | 12/1989 | Hoppough | |
| 4,938,209 A | 7/1990 | Fry | |
| 5,012,803 A | 5/1991 | Foley et al. | |
| 5,012,804 A | 5/1991 | Foley et al. | |
| 5,062,423 A | 11/1991 | Matson et al. | |
| 5,109,839 A | 5/1992 | Blasdell et al. | |
| 5,186,165 A | 2/1993 | Swann | |
| 5,231,982 A * | 8/1993 | Harrison et al. | 128/207.12 |
| 5,311,862 A * | 5/1994 | Blasdell et al. | 128/205.25 |
| 5,497,765 A | 3/1996 | Praud et al. | |
| 5,535,741 A * | 7/1996 | Widerstrom et al. | 128/206.21 |
| 5,586,551 A * | 12/1996 | Hilliard | 128/203.29 |
| 5,645,049 A * | 7/1997 | Foley et al. | 128/203.29 |
| D388,873 S * | 1/1998 | Richards et al. | D24/110.4 |
| 5,730,122 A * | 3/1998 | Lurie | 128/207.12 |
| 5,765,553 A | 6/1998 | Richards et al. | |
| 5,881,718 A * | 3/1999 | Mortensen et al. | 128/203.11 |
| 5,954,049 A * | 9/1999 | Foley et al. | 128/203.29 |
| 5,988,160 A * | 11/1999 | Foley et al. | 128/200.22 |
| 6,192,876 B1 | 2/2001 | Denyer et al. | |
| 6,206,003 B1 * | 3/2001 | Burch | 128/206.21 |

FOREIGN PATENT DOCUMENTS

| | | |
|---|---|---|
| AU | B-16114/92 | 11/1992 |
| CA | 1 220 111 | 4/1987 |
| CA | 1220111 | 4/1987 |
| CA | 2 092 614 | 4/1996 |
| DE | 726 282 | 10/1942 |
| DE | 30 00 518 | 1/1981 |
| EP | 0 139 363 A1 | 5/1985 |
| EP | 0 514 085 A1 | 12/1992 |
| EP | 0 601 708 A2 | 11/1993 |
| FR | 336.052 | 2/1904 |
| FR | 812.329 | 5/1937 |
| GB | 531805 | 1/1941 |
| GB | 2 230 456 A | 10/1990 |

* cited by examiner

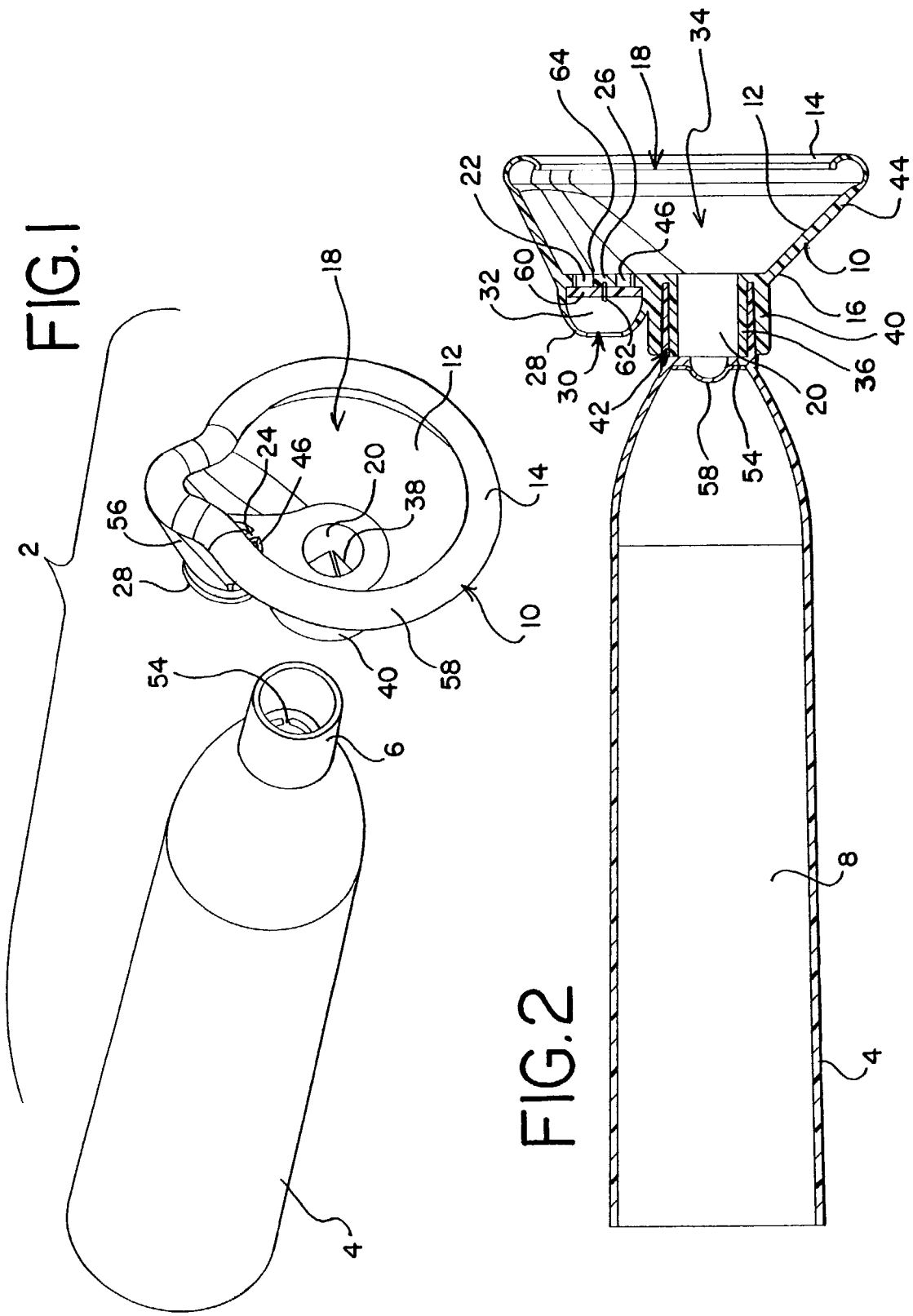

MASK WITH INHALATION VALVE

This application claims the benefit of U.S. Provisional Application Ser. No. 60/289,485, filed May 8, 2001, the entire disclosure of which is hereby incorporated by reference.

BACKGROUND

The invention relates generally to masks, and in particular, to a mask having an inhalation valve.

Masks are commonly used to administer various gases or substances in aerosol form. Typically, such masks include an inlet, which can be connected to a gas source or aerosol delivery device, such as a holding chamber or spacer, and an outlet, which is shaped to receive or fit over a portion of the face of the user. Often, the delivery device will include a one-way valve, which is actuated upon inhalation by the user. Alternatively, the inhalation valve is disposed in the inlet opening of the mask, and will open upon inhalation by the user so as to ensure that the gas or aerosolized substance is properly administered to the user. As such, the inhalation valve reduces the importance of coordination between actuation and inhalation. Typically, the inhalation valve is manufactured as a separate piece that is secured to the mask in the inlet thereof during the assembly process. As such, multiple parts must be made, inventoried and assembled. Other masks may also include an exhaust port, which is typically configured with an exhaust valve. Again, the valve is typically configured as a separate part.

SUMMARY

Briefly stated, one aspect of the invention is directed to a mask for use in inhaling a substance. The mask includes a mask housing defining a chamber. The housing has an inlet and an outlet communicating with the chamber. A valve is disposed in the inlet and is integrally formed with the housing, such that the valve and the housing are formed as a one-piece unit. In a preferred embodiment, the inhalation valve is a duck-bill valve.

In another aspect of the invention, a channel is formed around the inlet of the housing. A substance delivery device includes an output end that is disposed in the channel.

In another aspect of the invention, the housing further comprises an exhaust port. Preferably, the exhaust port is spaced from the inlet. In a preferred embodiment, an exhalation valve is disposed in the exhaust port.

In yet another aspect, the housing has an interior defining the chamber and an exterior. A shield is disposed around the exhaust port on the exterior of said housing. Preferably, the shield is integrally formed with the housing and inhalation valve.

In another aspect, a method of manufacturing a mask includes molding a one-piece mask comprising a mask housing defining a chamber and an inhalation valve. The housing includes an inlet and an outlet communicating with the chamber. The inhalation valve is disposed in the inlet and is integrally formed with the mask housing.

The present invention provides significant advantages over other masks. In particular, by forming the housing and inhalation valve as a one-piece unit, the mask can be made simpler and at lower cost, since separate parts and assembly are no longer required. In addition, the shield disposed around the exhalation valve further discourages the user and others from touching or otherwise handling the exhalation valve. As such, integrity of the exhalation valve is more easily maintained, and the mask is thereby made more robust. Moreover, the channel formed around the inlet provides a simple, robust structure for engaging the output end of a substance delivery device, such as an aerosol holding chamber.

The present invention, together with further objects and advantages, will be best understood by reference to the following detailed description taken in conjunction with the accompanying drawings.

BRIEF DESCRIPTION OF THE DRAWINGS

FIG. 1 is an exploded perspective view of a holding chamber and a mask.

FIG. 2 is a cross-sectional view of a holding chamber engaged with a mask.

DETAILED DESCRIPTION OF THE PRESENTLY PREFERRED EMBODIMENTS

Figure 3:
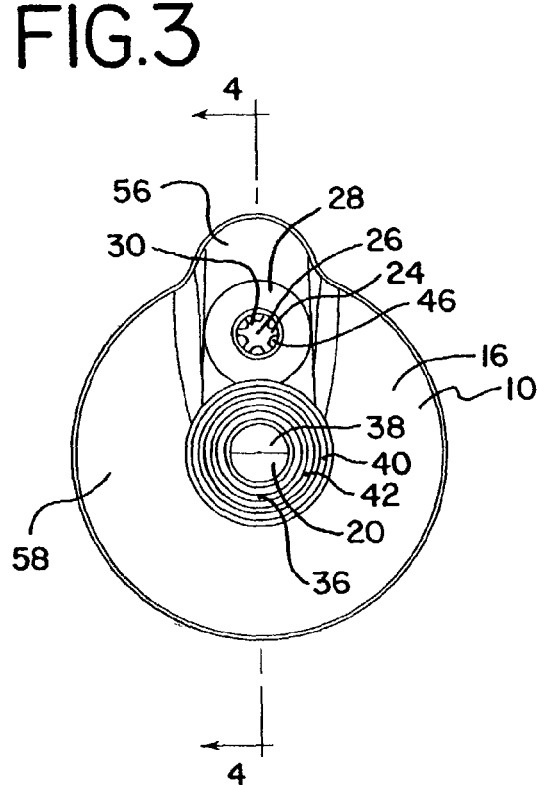
FIG. 3 is a front elevation view of one embodiment of a mask.

Referring to FIGS. 1 and 2, an apparatus 2 for delivering a substance to a user is shown as including a holding chamber 4 and a mask 10. It should be understood that the term "substance" means any gas, liquid or solid, including aerosols, and includes various medicines such as beta agonists, which are commonly administered by metered dose inhalers (MDI's) as disclosed in U.S. Pat. No. 5,645,049, which is hereby incorporated by reference. The mask 10 can be configured to be attached to any number of delivery devices, including aerosol delivery devices that comprise MDI's, or other apparatus that is suited to produce an aerosol or are attached to MDI's. Examples of these devices are holding chambers and spacers and delivery devices with an integrated actuator, such as the devices shown in U.S. application Ser. No. 09/287,997, filed Apr. 7, 1999, and entitled "Aerosol Medication Delivery Apparatus and System," which is hereby incorporated herein by reference.

Referring to FIGS. 2–6, the mask 10 includes a housing 44 having an exterior 16 and an interior 12 defining a chamber 34. The housing includes an upper portion 56 and a lower portion 58, which is generally conically shaped. The upper portion 56 is shaped to receive the nose of the user and forms in part the chamber 34. The housing 44 further includes a plurality of openings, including at least one inlet 20, at least one outlet 18 and at least one exhaust port 22. A bumper 14 is formed around a periphery of the outlet 18 and is adapted to engage the face of a user. It should be understood that the term "plurality" means two or more. The mask may include a plurality of inlets, outlets and exhaust ports. The exhaust port 22 is preferably spaced along the housing from the inlet 20 such that the inlet is not coaxial with the exhaust port.

The exhaust port 22 preferably includes an opening 46 having a plurality of spokes 24 extending radially from a center portion 26. The spokes 24 and a peripheral portion of the housing surrounding the opening 46 form a valve seat. An exhalation valve 60 is disposed over the opening 46 in the exhaust port. The exhalation valve 60 is preferably one-way, meaning that it permits the user to exhale and exhaust air from the interior of the housing to the exterior thereof, but does not permit air to enter into the chamber through the exhaust port. In one embodiment, the exhalation valve includes a valve head 64 that is seated on the valve seat, so as to prohibit air from entering the chamber through the exhaust port, and a stem 62 that is connected to the center portion 26. Alternatively, the exhalation valve can be configured as a one-way duckbill valve, which can be made separately from the housing, or can be integrally formed therewith. Various configurations of the exhalation valve are disclosed in U.S. Pat. Nos. 5,988,160 and 5,645,049, the entire disclosures of which are hereby incorporated herein by reference.

Referring to FIGS. 2–4 and 5, a shield 28 is formed on the exterior of the housing and extends around the exhaust port 22. The shield preferably forms a cavity 32 or chamber in which the exhalation valve is located. The shield 28 is preferably shaped as a "bubble," at least a portion of which is spherically shaped. The shield includes an inlet opening 30, which preferably has a smaller diameter than the exhaust port and which preferably is small enough so as to further discourage the user from inserting a finger into the cavity. The diameter of the inlet opening is preferably less than 10 mm. As noted above, the mask housing can include additional exhaust port openings suited for additional exhalation valves, and the illustration of a single valve is exemplary rather than limiting. The preferred embodiment is configured with only a single exhaust port 22, which is preferably located above the inlet 20 during the normal operation of the mask.

Figure 4:
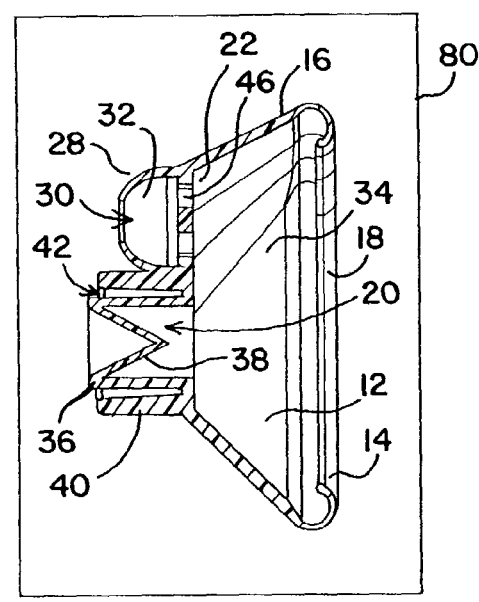
FIG. 4 is a cross-sectional view of the mask taken along line 4—4 in FIG. 3.

Referring to FIGS. 3 and 4, the mask further includes an inhalation valve 38 disposed in the inlet 20, which is preferably defined by a tube 36 that extends from the housing 44 and communicates with the chamber 34. In a preferred embodiment, the inhalation valve 38 is integrally molded with the mask housing 44 in the inlet 20. In a preferred embodiment, shown in FIG. 4, the mask housing 44, inhalation valve 38, exhaust port 22 and shield 28 can be integrally molded or formed as a one-piece unit or member from a substantially homogenous material. The one-piece mask is preferably injection molded. For example, a mold 80 can be used to form the mask. The mask housing 44, inhalation valve 38, exhaust port 22 and shield 28 be molded from any elastomeric material, including, without limitation, silicone, rubber and thermoplastic elastomers. The preferred material is silicone.

In alternative embodiments, the inhalation valve can also be affixed to the mask housing by other means, for example with adhesives or by heat sealing. The mask is intended for use with aerosol delivery devices that require an inhalation valve, which can be omitted from the delivery apparatus when the mask is configured with an inhalation valve. Alternatively, the inhalation valve component of the aerosol delivery device is located at the output end of the chamber component of the device. The output end typically will comprise a valve seat and a means of retaining the valve in place. The retaining means are generally located on the inside of a mouthpiece or mask adapter, which is attached to the output end of the chamber after the valve has been seated.

The inhalation 38 valve opens upon inhalation allowing the user to inhale the substance, such as an aerosol, retained in the chamber 8 of the holding chamber component of the aerosol delivery device. The inhalation valve 38 reduces the importance of coordination between actuation and inhalation, in that a device, such as an MDI, can be actuated to release a dose of substance into chamber 8, where it is retained until the user inhales the substance. As such, the user does not have to inhale at the same time they are actuating the device. The holding chamber 4 preferably includes a cylindrical tube 6 or outlet that extends from the output end and which engages and is connected to the mask 10. As shown in FIGS. 1 and 2, one embodiment of the housing includes an outer tube 40 formed circumferentially around the inlet tube 36, so as to form a groove or channel 42 therebetween. The cylindrical outlet tube 6 of the chamber is inserted into the circular channel 42 with a friction fit between the inner and outer tubes 36, 40. It should be understood that the chamber outlet tube 6 can be simply fitted around the inner tube 36, without the need for the outer tube. Preferably, the outer tube 40 is integrally formed or molded with the housing. In an alternative embodiment, the chamber tube has a diameter slightly less than the diameter of the inlet opening 20, such that the tube fits inside the inner tube 36 with a friction fit therebetween. Preferably, the diameter of the inlet 20, otherwise defined as the inner diameter of the tube 36, is about 10–30 mm, and more preferably about 16 mm, while the outer diameter of the inner tube 36 is preferably about 12–40 mm and more preferably about 20 mm, and in one preferred embodiment is about 19.93 mm. Preferably, the inlet tubes 36, 40 have lengths of about 10–44 mm, and preferably 22 mm and 20 mm respectively, while the valve preferably has a length of about 5–30 mm, and more preferably 16.27 mm.

By having the inhalation valve 38 integrally formed on the mask with the housing 44 as opposed to being a separate part connected to the mask or to the output end of the chamber, the number of parts is reduced because there is no need for a valve retaining means and/or a valve seat. As such, the manufacturing costs are reduced, and the parts can be assembled faster and at less cost. Moreover, since the inhalation valve is preferably integrally molded with the housing, the valve cannot be removed or displaced by the user without considerable effort. In addition, the mask can be sold as a standalone product for use when an inhalation valve may be required depending on the type of usage or therapy.

As shown in FIGS. 3 and 4, in a preferred embodiment, the inhalation valve 38 is configured as a duck bill valve, which includes opposing flaps that extend from the inner tube 36 and points downstream within the inlet. The duckbill valve is particularly well suited for this application since a duckbill valve is self sealing, robust and does not require valve seating when integrally formed with the mask housing.

Figure 5:
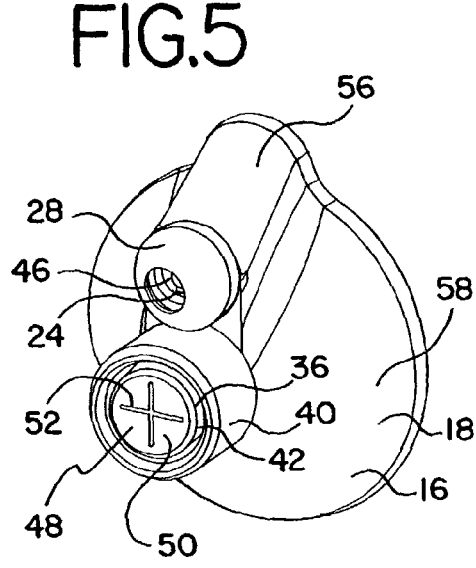
FIG. 5 is a front perspective view of an alternative embodiment of the mask.
Figure 6:
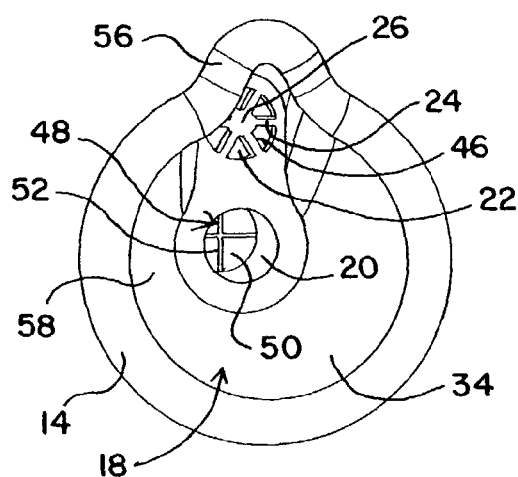
FIG. 6 is a rear perspective view of the mask shown in FIG. 5.

In an alternative embodiment, shown in FIGS. 5 and 6, the inhalation valve 48 includes a plurality of valve flaps 50, shown as four, which are separated by slits 52. The valve flaps 50 fold inward or downstream upon inhalation. Upon exhalation, the valve flaps 50 are seated on a valve seat 54 formed in the output end of the holding chamber 4. The valve seat can include a baffle 68 having a convex surface 70, or alternatively a concave surface, which faces upstream.

The mask is preferably produced in three different sizes. One size suited for use by infants, the other for children, and the last one for adults.

In operation, the inlet 20 of the mask 10 is attached to the output end of an aerosol delivery device, shown as the holding chamber 4. It should be understood that the inlet alternatively could be operably connected with a gas line or other like delivery component. The user adjusts the mask onto his/her face, with a portion of the user's face, including for example the nose and mouth, disposed through and in the outlet 18 and extending into the chamber 34. The user then actuates the MDI canister, or other device that holds the substance, and thereby produces an aerosol or releases a gas or other substance that is discharged into the holding chamber 4. The user then begins inhalation at which time the inhalation valve 38 opens and allows the substance to enter the chamber 34. The substance then exits the mask as it enters into the user's mouth or nasal passageways and ultimately into the user's respiratory tract. During inhalation, the exhalation valve 60 seals shut, with the valve head engaging the valve seat, so as to not allow any ambient air to enter into the mask chamber 34. The user then exhales at which time the inhalation valve 38 seals shut not allowing any exhaled gases to enter the holding chamber 4. At the same time, the exhalation valve 60 opens allowing the exhaled gases to exit through the exhaust port 22 and into the ambient air. Many therapies generally require the user to inhale and exhale a number of times. Accordingly, it may be important for the user to cyclically inhale and exhale while keeping the mask on at all times. This is achieved by having the exhalation valve 60 disposed in the mask. The mask 4 can be retained on the user's head using a strap or other device (not shown).

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A mask for use in inhaling a substance comprising:
    a mask housing defining a chamber and having an inlet and an outlet communicating with said chamber; and
    an inhalation valve disposed in said inlet and integrally formed with said mask housing, wherein said valve and said mask housing are formed as a one-piece unit, wherein said inhalation valve is moveable between open and closed positions, and wherein said inhalation valve is positioned entirely exteriorly to said chamber and does not extend into said chamber when positioned in said open and closed positions.

2. The mask of claim 1 wherein said valve is a one-way duckbill valve.

3. The mask of claim 1 wherein said mask housing further comprises an exhaust port, wherein said exhaust port is spaced from said inlet.

4. The mask of claim 3 further comprising an exhalation valve disposed in said exhaust port.

5. The mask of claim 1 wherein said mask housing and said inhalation valve are formed from a single homogeneous piece of material.

6. The mask of claim 1 wherein said inlet comprises a cylindrical tube, wherein said chamber is defined at least in part by a wall, wherein at least a portion of said wall of said chamber flares outwardly from an end of said cylindrical tube, and wherein said inhalation valve is formed entirely within said cylindrical tube and does not extend into said chamber.

7. A mask for use in inhaling a substance comprising:
    a mask housing defining a chamber and having an inlet and an outlet communicating with said chamber, said inlet defined by a first tubular wall, wherein said housing further comprises a channel formed around an outer surface of said inlet between said first tubular wall and a second tubular wall, wherein said second tubular wall is formed circumferentially around said first tubular wall in a radially spaced apart relationship therewith; and
    an inhalation valve disposed in said inlet and integrally formed with said mask housing, wherein said valve and said mask housing are formed as a one-piece unit.

8. The mask of claim 7 further comprising a holding chamber comprising an outlet tube inserted into said channel.

9. A method of manufacturing an apparatus for delivering a substance to a user, the method comprising:
    molding a one-piece mask comprising a mask housing defining a chamber and having an inlet and an outlet communicating with said chamber and an inhalation valve disposed in said inlet and integrally formed with said mask housing, wherein said inhalation valve is moveable between open and closed positions, and wherein said inhalation valve is positioned entirely exteriorly to said chamber and does not extend into said chamber when positioned in said open and closed positions.

10. The method of claim 9 wherein said inhalation valve is a one-way duckbill valve.

11. The method of claim 9 wherein said mask housing further comprises an exhaust port, wherein said exhaust port is spaced from said inlet.

12. The method of claim 11 further comprising disposing an exhalation valve in said exhaust port.

13. The method of claim 9 wherein said one-piece mask is made of silicone.

14. The method of claim 9 wherein said molding said one-piece mask comprises integrally forming said mask housing and said inhalation valve as a single homogeneous piece of material.

15. The method of claim 9 wherein said inlet comprises a cylindrical tube, wherein said chamber is defined at least in part by a wall, wherein at least a portion of said wall of said chamber flares outwardly from an end of said cylindrical tube, and wherein said inhalation valve is formed entirely within said cylindrical tube and does not extend into said chamber.

16. A method of manufacturing an apparatus for delivering a substance to a user, the method comprising:
    molding a one-piece mask comprising a mask housing defining a chamber and having an inlet and an outlet communicating with said chamber and an inhalation valve disposed in said inlet and integrally formed with said mask housing, said inlet defined by a first tubular wall, wherein said molding said one-piece mask comprises forming a channel around an outer surface of said inlet between said first tubular wall and a second tubular wall, wherein said second tubular wall is formed circumferentially around said first tubular wall in a radially spaced apart relationship.

17. The method of claim 11 further comprising inserting an output end of a delivery device into said channel.

18. The method of claim 16 further comprising inserting an outlet tube of a holding chamber into said channel.

19. A mask for use in inhaling a substance comprising:
    a mask housing defining a chamber and having an inlet tube and an outlet communicating with said chamber;
    an inhalation valve disposed in said inlet tube and integrally formed with said mask housing, wherein said valve and said mask housing are formed as a one-piece unit; and a holding chamber comprising an outlet tube circumferentially disposed around said inlet tube wherein at least a portion of said inhalation valve is disposed in said outlet tube.

20. The mask of claim 19 wherein said holding chamber further comprises a valve seat engaging said inhalation valve when said inhalation valve is in a closed position.

21. A method of manufacturing an apparatus for delivering a substance to a user, the method comprising:

molding a one-piece mask comprising a mask housing defining a chamber and having an inlet tube and an outlet communicating with said chamber and an inhalation valve disposed in said inlet tube and integrally formed with said mask housing; and inserting an outlet tube of a holding chamber circumferentially around said inlet tube of said mask housing wherein said inhalation valve is disposed in said outlet tube.

22. The method of claim 21 wherein said holding chamber further comprises a valve seat engaging said inhalation valve when said inhalation valve is in a closed position.

* * * * *

UNITED STATES PATENT AND TRADEMARK OFFICE
CERTIFICATE OF CORRECTION

PATENT NO. : 7,013,896 B2  Page 1 of 1
APPLICATION NO. : 10/139992
DATED : March 21, 2006
INVENTOR(S) : James N. Schmidt It is certified that error appears in the above-identified patent and that said Letters Patent is hereby corrected as shown below:

In the Claims

Column 6, claim 17, line 55, after "The method of claim" replace "11" with --16--.

Signed and Sealed this

Seventh Day of September, 2010

David J. Kappos
*Director of the United States Patent and Trademark Office*